United States Patent [19]

Sakai et al.

[11] 4,297,426
[45] Oct. 27, 1981

[54] ELECTROPHOTOGRAPHIC ELEMENT WITH CARBAZOLE HYDRAZONE OR ANILE CHARGE TRANSPORT COMPOUNDS

[75] Inventors: Kiyoshi Sakai; Mitsuru Hashimoto, both of Numazu; Tomiko Kawakami, Tokyo, all of Japan

[73] Assignee: Ricoh Co., Ltd., Tokyo, Japan

[21] Appl. No.: 152,069

[22] Filed: May 21, 1980

[30] Foreign Application Priority Data

May 28, 1979 [JP] Japan .................................. 54-65741
May 28, 1979 [JP] Japan .................................. 54-65742

[51] Int. Cl.³ .......................... G03G 5/06; G03G 5/14
[52] U.S. Cl. ..................................... 430/59; 430/58; 430/79; 430/96
[58] Field of Search ..................... 430/58, 59, 79, 96

[56] References Cited

U.S. PATENT DOCUMENTS 3,870,516 3/1975 Smith et al. ................. 430/58 X
4,134,761 1/1979 Okazaki et al. .................. 430/59
4,192,677 3/1980 Okazaki et al. .................. 430/59

FOREIGN PATENT DOCUMENTS 1599 2/1979 European Pat. Off. ............. 430/59
930988 7/1958 United Kingdom ................ 430/73

Primary Examiner—Roland E. Martin, Jr.
Attorney, Agent, or Firm—Blanchard, Flynn, Thiel, Boutell & Tanis

[57] ABSTRACT

An electrophotographic element comprising a conductive substrate and a mono-layer type or multi-layer type photosensitive layer, superposed thereon, containing a photoconductive material in which said photoconductive material is a hydrazone compound having the following general formula (I) or an anile compound having the following general formula (II):

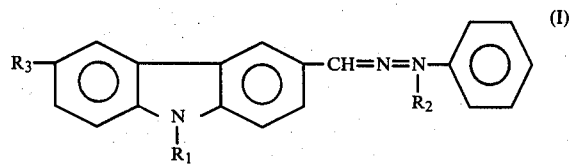

[where $R_1$ is a methyl, ethyl 2-hydroxyethyl or 2-chloroethyl group; $R_2$ is a methyl, ethyl, benzyl or phenyl group; and $R_3$ is chlorine, bromine, a $C_1$-$C_4$ alkyl group, a $C_1$-$C_4$ alkoxy group, a dialkylamino group with $C_1$-$C_4$ alkyl or a nitro group.]

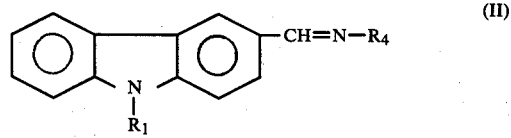

[where $R_1$ is the same as the said general formula (I); and $R_4$ is a substituted or non-substituted phenyl, naphthyl, heterocyclic or $C_1$-$C_{10}$ alkyl group.]

17 Claims, 3 Drawing Figures

ELECTROPHOTOGRAPHIC ELEMENT WITH CARBAZOLE HYDRAZONE OR ANILE CHARGE TRANSPORT COMPOUNDS

BACKGROUND OF THE INVENTION

1. Field of the invention

This invention relates in general to a mono-layer type or multi-layer type electrophotographic element, and in particular to a novel electrophotographic element having a photosensitive layer containing as an available ingredient a hydrazone compound having the following general formula (I) or an anile compound having the following general formula (II):

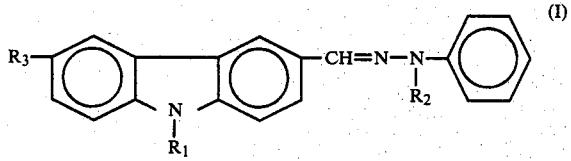

[where $R_1$ is a methyl, ethyl, 2-hydroxyethyl or 2-chloroethyl group; $R_2$ is a methyl, ethyl, benzyl or phenyl group; and $R_3$ is chlorine, bromine, a $C_1$–$C_4$ alkyl group, a $C_1$–$C_4$ alkoxy group, a dialkylamino group with $C_1$–$C_4$ alkyl or a nitro group.]

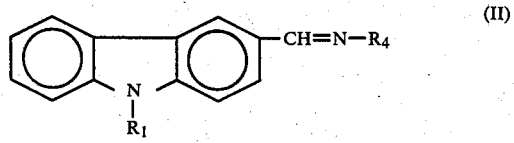

[where $R_1$ is the same as the said general formula (I); and $R_4$ is a substituted or non-substituted phenyl, naphthyl, heterocyclic or $C_1$–$C_{10}$ alkyl group.]

As the substitution groups for the substituted phenyl referred to in the general formula (II) there can be enumerated $C_1$–$C_4$ alkyl group, $C_1$–$C_4$ alkoxy group, dialkylamino group with $C_1$–$C_4$ alkyl, hydroxy group, etc. And, the heterocyclic group referred to in the general formula (II) includes pyridyl, benzothiazolyl and the like.

2. Description of the Prior Art

Inorganic substances such as selenium, cadmium sulfide, zinc oxide, etc. have hitherto been utilized as photoconductive materials for use in elements in electrophotographic processes. In this context, it is to be noted that the "electrophotographic process" referred to herein generally denotes one of the image forming methods which comprise the steps of electrifying a photoconductive element in the dark first of all for instance with corona discharge or the like, then exposing the element to light in an imagewise manner to selectively dissipate the charge from only the light struck portions of the element thereby forming a latent image and rendering the latent image visible by means of a developing process utilizing an electroscopic fine powder comprising a coloring agent called a toner such as dye, pigment or the like and a binder resin such as resin, high molecular substance or the like thereby forming a visible image. The element adapted for the above-mentioned electrophotographic process is required to possess the following fundamental characteristics: (1) capability of being charged with a suitable potential in the dark, (2) low discharge rate in the dark, (3) rapid dischargeability upon light radiation and so forth. The hitherto utilized inorganic substances as enumerated above surely possess a number of merits, but at the same time possess various demerits. For instance, the now universally utilized selenium can satisfy the aforesaid requirements (1) to (3) to a sufficient degree, but is defective in that it is manufactured with difficulty and consequently the manufacturing cost is high. In addition, the selenium is defective in that it is difficult to process the selenium, which has no flexibility, into a belt, close attention must be paid in handling the selenium which is very sensitive to mechanical impacts and the like. On the other hand, the cadmium sulfide and zinc oxide are utilized in the element in the manner of their being dispersed in a binder resin. However, such element lacks the mechanical characteristics such as smoothness, hardness, tensile strength, frictional resistance, and therefore it can not stand repeated use.

In recent years, electrophotographic elements employing various kinds of organic substances have been proposed in order to remove the drawbacks inherent in the inorganic substances as enumerated above. Some of said elements are put to practical use, for instance, such as the element including poly-N-vinylcarbazole and 2,4,7-trinitrofluorene (U.S. Pat. No. 3,484,237), the element including poly-N-vinylcarbazole sensitized with a pyrylium salt type pigment (Japanese Patent Publication No. 25658/1973), the element including an organic pigment as the principal ingredient (Japanese Laid-open Patent Application No. 37543/1972), the element including a cocrystalline complex consisting of dye and resin as the principal ingredient (Japanese Laid-open Patent Application No. 10735/1972), etc. However, the fact is that these elements surely are considered to possess superior characteristics as well as high practical values, but, when taking into consideration various requirements for elements, can not meet these requirements yet to a satisfactory degree.

On the other hand, it is perceived that these excellent elements, though there is a difference therebetween depending on their objects or manufacturing processes, can generally exhibit superior characteristics as a result of incorporating high-efficient photoconductive materials therein.

SUMMARY OF THE INVENTION

We have made a series of studies on the photoconductive material of this kind to discover the fact that said hydrazone compound having the general formula (I) or said anile compound having the general formula (II) acts effectively as the photoconductive material for electrophotographic elements. In other words, we have discovered that the hydrazone compound (I) or the anile compound having the general formula (II), as mentioned subsequently, can provide, when combined with various kinds of materials, elements which can exhibit unexpectedly superior effects and are rich in surprisingly versatile usability.

The hydrazone compound having the general formula (I) or the anile compound having the general formula (II) suitably used for this invention is prepared in any usual manner, in other words, in the manner of causing a condensation reaction between equimolecular weights of 3-formyl carbazoles and phenylhydrazines [in the case of the general formula (I)] or amines [in the case of the general formula (II)] in alcohol, if needed, by adding a small quantity of acid (glacial acetic acid or mineral aicd). There are instances where said hydrazines or amines preferably should be used in slightly excess quantities at the time of condensation reaction for the purpose of facilitating the purification of raw reaction products.
As the compounds corresponding to the general formula (I) there can be enumerated the following ones.
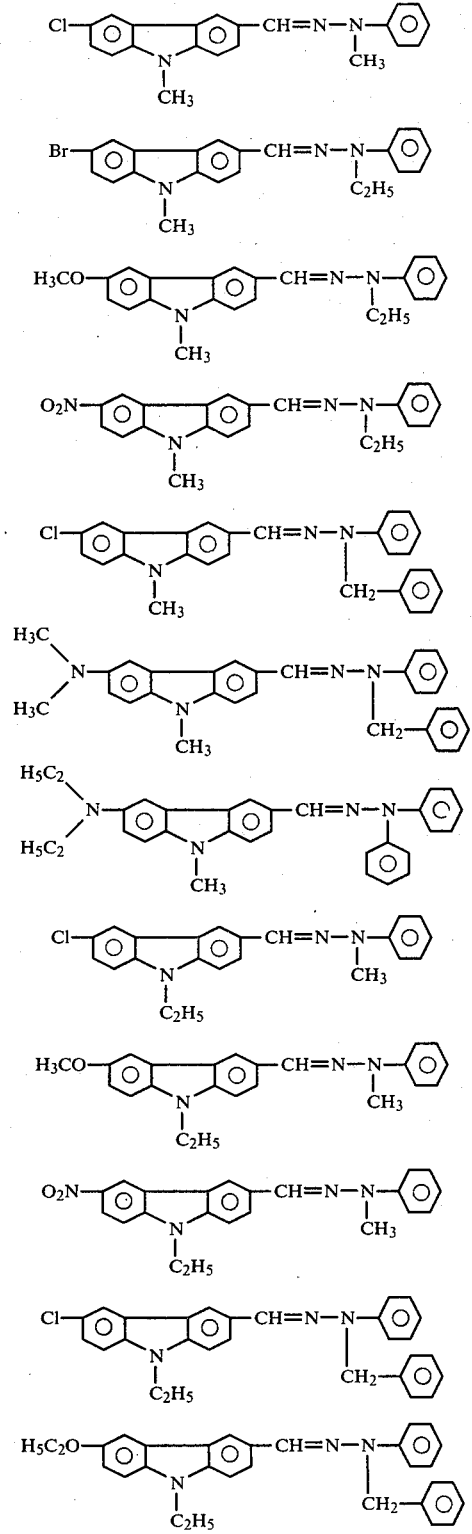
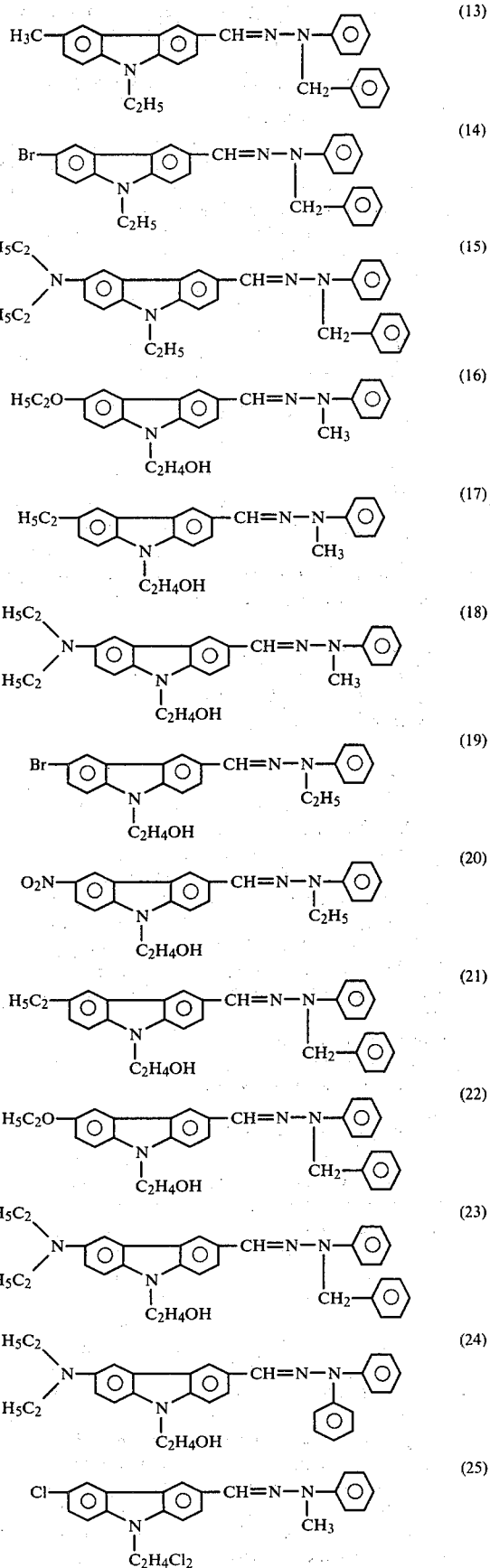

As the compounds corresponding to the general formula (II), furthermore, there can be enumerated the following ones.

-continued

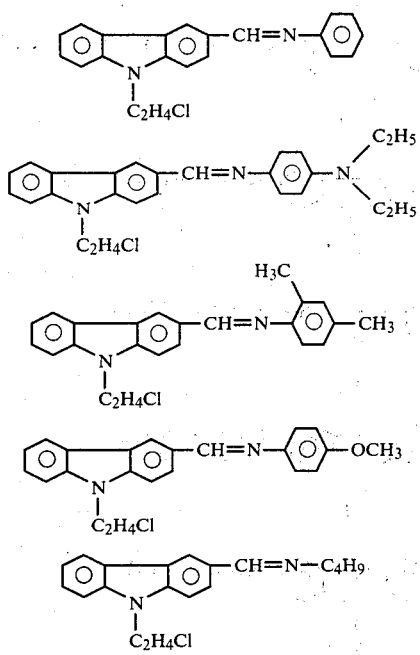

Figure 1:
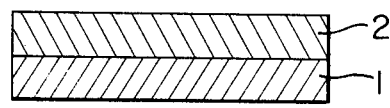
FIGS. 1 and 2 are each an enlarged cross-sectional view of a mono-layer type electrophotographic element according to this invention.

The reference numerals in the drawings identify the following members:

1 . . . conductive substrate
2,2',2" . . . photosensitive layer
3 . . . charge generation material
4 . . . charge transport medium
5 . . . charge generation layer
6 . . . charge transport layer.

Figure 2:
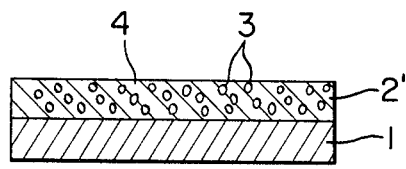
Figure 3:
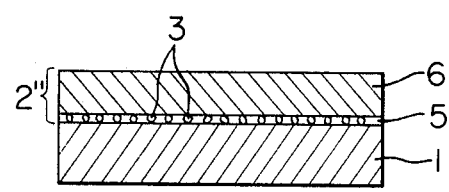
FIG. 3 is an enlarged cross-sectional view of a multi-layer type electrophotographic element according to this invention.

The electrophotographic elements according to this invention, which include the above defined hydrazone compounds or anile compounds, can take the forms illustrated in FIGS. 1 to 3 depending upon how these hydrazone compounds or anile compounds are applied. The element illustrated in FIG. 1 comprises a conductive substrate 1 and a photosensitive layer 2 adjacent the substrate, the photosensitive layer consisting essentially of a hydrazone compound (I) or anile compound (II), a sensitizing dye and a binder resin. The element illustrated in FIG. 2 comprises a conductive substrate 1 and a photosensitive layer 2' adjacent the substrate, the photosensitive layer 2' being formed by dispersing a charge generation material 3 in a charge transport medium comprising a hydrazone compound (I) or an anile compound (II) (these are sometimes called a charge transport material respectively) and a binder resin. The element illustrated in FIG. 3 comprises a conductive substrate 1 and a photosensitive layer 2" adjacent the substrate, the photosensitive layer 2" being comprised of a charge generation layer 5 which is essentially a charge generation material 3 and a charge transport layer 6 including a hydrazone compound (I) or an anile compound (II).

In the element of FIG. 1, the hydrazone compound (I) or the anile compound (II) functions as a photoconductive material and therefore the generation and transportation of charges required for light decay is effected through the hydrazone compound or anile compound. However, as the hydrazone compound (I) or the anile compound (II) is scarcely absorptive to visible light region, in case where it is utilized for the purpose of forming an image by means of visible light, it must be sensitized with a sensitizing dye being adsorptive to visible light region.

In the case of the element of FIG. 2, the hydrazone compound (I) or the anile compound (II) forms a charge transport media in conjunction with a binder (and a plasticizer as occasion demands), while the charge generation material such as an inorganic or organic pigment generates charges. In this case, the main ability of the charge transport media is to accept charges that the charge generation material generates and to transport the charges. It is fundamentally required in this instance that the absorption wave length regions of both the charge generation material and the hydrazone compound (I) or anile compound (II) should not overlap each other mainly in the visible light region. This is because there is the necessity for permitting light to transmit up to the surface of the charge generation material so that the latter may generate charges efficiently. The hydrazone compound (I) or anile compound (II) according to this invention is characterized in that it is scarcely absorptive to the visible light region and generally acts as the charge transport material effectively especially when combined with the charge generation material capable of generating charges upon absorption of light in the visible region.

In the case of the element illustrated in FIG. 3, the light transmitted through the charge transport layer 6 reaches the charge generation layer 5 to thereby generate charges at the light struck portions thereof, while the thus generated charges are injected in the charge transport layer 6 and transported therethrough. The mechanism employed herein that the generation of charges required for light decay is allotted to the charge generation material, while the transportation of the charges is allotted to the charge transport medium (the hydrazone compound (I) or the anile compound (II) of this invention mainly acts for that purpose) is the same as that employed in the element illustrated in FIG. 2. The hydrazone compound (I) or the anile compound (II) acts as the charge transport material herein, too.

The element illustrated in FIG. 1 may be prepared by coating a solution onto a conductive substrate and drying, said solution being obtained by dissolving a hydrazone compound (I) or an anile compound (II) in a binder solution and further adding a sensitizing dye thereto as occasion demands.

The element illustrated in FIG. 2 may be prepared by coating a dispersion onto a conductive substrate and drying, said dispersion being obtained by dispersing fine particles of a charge generation material in a solution containing dissolved therein a hydrazone compound (I) or an anile compound (II) and a binder. The element illustrated in FIG. 3 may be prepared by vacuum-evaporating a charge generation material onto a conductive substrate or coating onto a conductive substrate a dispersion obtained by dispersing fine particles of the charge generation material, if needed, in a suitable solvent containing dissolved therein a binder, then by coating a solution containing a hydrazone compound (I)

or an anile compound (II) and a binder onto the resulting charge generation layer and, if further needed, after surface finishing or film thickness regulation by, for instance, buffing or the like, and drying. The coating method used herein includes usual means, for instance, such as doctor blade, wire bar and the like.

The photosensitive layers of the elements illustrated in FIGS. 1 and 2 are each between about 3 microns and 50 microns thick, preferably between about 5 microns and 20 microns thick. In the case of the element illustrated in FIG. 3, the charge generation layer is about 0.01 to 5 microns thick, preferably about 2 microns or less thick, and the charge transport layer is between about 3 microns and 50 microns thick, preferably between about 5 microns and 20 microns thick. In the case of the element illustrated in FIG. 1 the percentage of the hydrazone compound (I) or anile compound (II) contained in the photosensitive layer is in the range of from about 30 to 70% by weight, preferably about 50% by weight relative to the photosensitive layer. The percentage of the sensitizing dye used for rendering the photosensitive layer sensitive to the visible region is in the range of from about 0.1 to 5% by weight, preferably from about 0.5 to 3% by weight relative to the photosensitive layer. In the element illustrated in FIG. 2, the percentage of the hydrazone compound (I) or anile compound (II) to the photosensitive layer is in the range of from about 10 to 95% by weight, preferably from about 30 to 90% by weight, and the percentage of the charge generation material to the photosensitive layer is in the range of from about 0.1 to 50% by weight, preferably about 20% by weight or less. In the element illustrated in FIG. 3, the percentage of the hydrazone compound (I) or anile compound (II) to the charge transport layer, like the case of the photosensitive layer in the element of FIG. 2, is in the range of from about 10 to 95% by weight, preferably from about 30 to 90% by weight. In this context, it is to be noted that a plasticizer may be used in conjunction with a binder in the preparation of the respective elements illustrated in FIGS. 1 to 3.

In the case of the element according to this invention, as the conductive substrate there can be employed a metallic plate or foil of aluminum or the like, an aluminum or the like evaporation deposited plastic film, a conductively treated paper or the like. As the binder suitably used for this invention there may be enumerated condensation resins such as polyamide, polyurethane, polyester, epoxy resin, polyketone, polycarbonate, etc., vinyl polymers such as polyvinyl ketone, polystyrene, poly-N-vinylcarbazole, polyacrylamide, etc., and the like. However, it is to be noted that any insulating as well as adhesive resin may be employed. As the plasticizer for use in this invention there may be enumerated paraffin halide, polybiphenyl chloride, dimethylnaphthalene, dibutyl phthalate and so forth. The sensitizing dyes suitably used in the element of FIG. 1 include triarylmethane dyes such Brilliant Green, Victoria Blue B, Methyl Violet, Crystal Violet, Acid Violet 6B and the like; Xanthene dyes such as Rhodamine B, Rhodamine 6G, Rhodamine G Extra, Eosine S, Erythrosine, Rose Bengale, fluorescene and the like; thiazine dyes such as Methylene Blue and the like; cyanine dyes such as cyanine and the like; pyrylium dyes such as 2,6-diphenyl-4-(N,N-dimethylaminophenyl) thiapyrylium perchlorate, benzo pyrylium salt disclosed in Japanese Patent Publication No. 25658/1973 and the like; and so forth. The charge generation materials for use in the elements of FIGS. 2 and 3 include azo pigments comprised of inorganic pigments such as selenium, selenium-tellurium, cadmium sulfide, cadmium sulfide-selenium, etc. and organic pigments such as CI Pigment Blue-25 (CI 21180), CI Pigment Red 41 (CI 21200), CI Acid Red 52 (CI 45100), CI Basic Red 3 (CI 45210), the azo pigment having a carbazole skeleton (U.S. Ser. No. 872,679), the azo pigment having a styryl stilbene skeleton (U.S. Ser. Nos. 898,130 and 961,963), the azo pigment having a triphenylamine skeltone (U.S. Ser. No. 897,508), the azo pigment having a dibenzothiophene skeleton (U.S. Ser. No. 925,157), the azo pigment having an oxadiazole skeleton (U.S. Ser. No. 908,116), the azo pigment having a fluorenone skeleton (U.S. Ser. No. 925,157), the azo pigment having a bisstilbene skeleton (U.S. Ser. No. 922,526), the azo pigment having a distyryloxadiazole skeleton (U.S. Ser. No. 908,116), the azo pigment having a distyrylcarbazole skeleton (U.S. Ser. No. 921,086), etc.; phthalocyanine type pigments such as CI Pigment Blue 16 (CI 74100), etc.; indigo type pigments such as CI Bat Brown 5 (CI 73410), CI Bat Dye (CI 73030), etc.; perylene type pigments such as Argoscarlet B (available from Bayer Company), Indanthrene Scarlet R (available from Bayer Company) and so forth.

In this connection, it is to be noted that any one of the thus obtained elements can provide an adhesive or barrier layer, if needed, between the conductive substrate and the photosensitive layer. The materials suitably available for said adhesive or barrier layer include polyamide, nitrocellulose, aluminum oxide, etc., and preferably the film of said layer is 1 micron or less thick.

The copying process using the element of this invention comprises electrifying the surface of the element, exposing the same to light, thereafter developing and, if needed, transferring the thus formed image to another surface, such as paper.

The element according to this invention is advantageous in that it is generally of a high sensitivity and rich in flexibility.

DESCRIPTION OF THE PREFERRED EMBODIMENTS

Example 1

To 2 parts of Dian Blue (CI 21180) were added 98 parts of tetrahydrofuran. The resulting mixture was pulverized and mixed in a ball mill, thereby obtaining a charge generation pigment solution. This solution was coated onto an aluminum evaporation deposited polyester film by means of a doctor blade and air-dried thereby to form a 1 micron-thick charge generation layer. Subsequently, a charge transport layer forming solution was obtained by mixing 2 parts of hydrazone having the structural formula 17, 3 parts of polycarbonate resin (available under the Trademark Panlite L from TEIJIN) and 45 parts of tetrahydrofuran and well dissolving. This solution was coated onto said charge generation layer by means of a doctor blade and the same was dried at 100° C. for 10 minutes, thereby forming a charge transport layer being about 10 minutes thick. The instant element was thus prepared. This element was subjected to −6 KV corona discharge for 20 seconds by means of an electrostatic copying paper tester (SP 428 type available from KAWAGUCHI DENKI SEISAKUSHO K.K.) and charged negatively. Thereafter, the negatively charge element was left standing in the dark for 20 seconds for measuring the surface potential Vpo (V) at that time, and then was exposed to light from a tungsten lamp so that the surface intensity became 20 lux. Thus, the time (second) required until the surface potential was reduced to half of Vpo was calculated to determine the exposure amount E1/2(lux·sec). The obtained results showed: Vpo = −670 V and E1/2 = 3.3 lux·sec.

Example 2

A solution consisting of 3 parts of

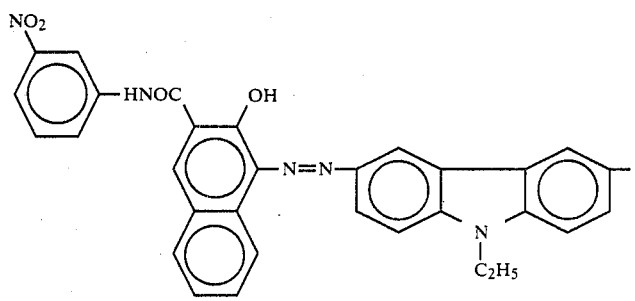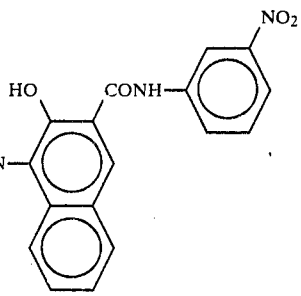

1 part of polyester resin (Polyester Adhesive 49000 available from du Pont) and 96 parts of tetrahydrofuran was pulverized and mixed in a ball mill, thereby obtaining a charge generation pigment dispersion. This dispersion was coated onto an aluminum evaporation deposited polyester film by means of a doctor blade, and the same was dried for 5 minutes in a drying machine heated to 80° C., thereby forming a 1 micron-thick charge generation layer. Subsequently, a charge transport layer forming solution was obtained by mixing 2 parts of hydrazone having the structural formula 5, 3 parts of polycarbonate resin (available under the trademark Panlite L from TEIJIN) and 45 parts of tetrahydrofuran and dissolving. This solution was coated onto said charge generation layer by means of a doctor blade and the same was dried at 100° C. for 10 minutes, thereby forming a charge transport layer being about 10 microns thick. The element of this invention was thus obtained.

This element was charged negatively as in Example 1 and measured as to Vpo and E1/2 respectively with the results: Vpo = −670 V and E1/2 = 9.1 lux·sec.

Example 3 and 4

The same procedure as Example 2 was repeated with the exception that the charge generation pigment and the charge transport material were replaced. The thus obtained results are as shown in Table 1.

TABLE 1

| Ex. | Charge generation pigment | Charge transport material | Vpo | E½ |
|---|---|---|---|---|
| 3 | H$_3$CO—⟨O⟩—HNOC OH ... —N=N—⟨O⟩—N—⟨O⟩—N=N— ... HO CONH—⟨O⟩—OCH$_3$ (with pendant —N=N— to naphthol-CONH—⟨O⟩—OCH$_3$) | 20 | 1270 V | 7.5 lux·sec |
| 4 | CH$_3$ / H$_3$C—⟨O⟩—HNOC OH —N=N—⟨O⟩—CH=CH—⟨O⟩—CH=CH—⟨O⟩—N=N— HO CONH—⟨O⟩—CH$_3$ (with H$_3$C) | 28 | 890 V | 6.8 lux·sec |

Example 5

The elements obtained according to Example 1 through 4 were charged negatively by means of a commercially available copying machine. The thus charged elements were then exposed through an original to light, thereby permitting an electrostatic latent image to be formed thereon. This electrostatic latent image was developed using a positively charged toner-containing dry developer. The thus developed image was electrostatically transferred onto the surface of paper (wood free paper) and fixed, whereby a clear-cut image was obtained. A clear-cut image was obtained likewise in the case of using a wet developer.

Example 6

Selenium was applied onto an about 300 microns-thick aluminum plate by means of vacuum evaporation method so as to be 1 micron thick, thereby forming a charge generation layer. Subsequently, 2 parts of hydrazone having the structural formula 9, 3 parts of polyester resin (Polyester Adhesive 49000 available from du Pont) and 45 parts of tetrahydrofuran were mixed and dissolved to thereby obtain a charge transport layer forming solution. This solution was coated onto the said charge generation layer (selenium evaporation deposited layer) by means of a doctor blade, air-dried and then dried again at reduced pressure to form thereon a charge transport layer being about 10 microns thick. The element of this invention was thus obtained.

This element was measured as to Vpo and E1/2 in accordance with the same procedure as that of Example 1 with the results: $Vpo = -910$ V and $E1/2 = 9.5$ lux·sec.

Example 7

In place of the selenium of Example 6 there was employed a perylene type pigment having the following formula:

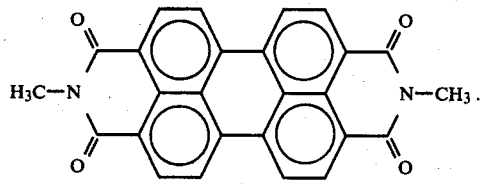

This pigment was coated onto the plate by means of vacuum evaporation method so as to be 0.3 micron thick, thereby forming a charge generation layer. Subsequently, an element similar to that of Example 6 was prepared with the exception that a charge transport material having the structural formula (9) was employed. This element showed the results: $Vpo = -670$ V and $E1/2 = 5.1$ lux·sec.

Example 8

The elements obtained according to Example 6 and Example 7 were charged negatively by means of a commercially available copying machine. The thus charged elements were then exposed through an original to light, thereby permitting an electrostatic latent image to be formed thereon. This electrostatic latent image was developed using a positively charged toner-containing dry developer. The thus developed image was electrostatically transferred onto the surface of paper (wood free paper) and fixed, whereby a clear-cut image was obtained. A clear-cut image was obtained likewise in the case of using a wet developer.

Example 9

A mixture of 1 part of Chlor Dian Blue and 158 parts of tetrahydrofuran was pulverized and mixed in a ball mill. Subsequently, the thus treated mixture was added with 12 parts of hydrazone compound having the structural formula 29 and 18 parts of polyester resin (Polyester Adhesive 49000 available from du Pont) and subjected to further mixing, thereby obtaining a photosensitive layer forming solution. This solution was coated onto an aluminum evaporation deposited polyester film by means of a doctor blade and the same was dried at 100° C. for 30 minutes to thereby form a photosensitive layer being about 16 microns thick. The element of this invention was thus obtained.

This element was positively charged with +6 KV discharge using the same device as that employed in Example 1 and likewise measured as to Vpo and E1/2 with the results: $Vpo = 710$ V and $E1/2 = 15.7$ lux·sec.

Example 10 through 12

Elements were prepared in accordance with the element preparation method similar to Example 9 with the exception that the charge generation pigment and charge transport material were replaced by those as shown in Table 2. These elements were subjected to the measurements similar to Example 1. The obtained results were as shown in Table 2.

TABLE 2

| Example | Charge generation pigment | Charge transport material | Vgo | E½ |
|---|---|---|---|---|
| 10 | Cl-[structure with HNOC, OH, N=N, N—N, O, N=N, HO, CONH, Cl] | (1) | V 690 | lux . sec 8.5 |
| 11 | [structure with HNOC, OH, N=N, fluorenone, N=N, HO, CONH] | (18) | 870 | 10.7 |

TABLE 2-continued

| Example | Charge generation pigment | Charge transport material | Vgo | E½ |
|---|---|---|---|---|
| 12 | H₃C—[pyrazolone]—N=N—⟨φ⟩—N—⟨φ⟩—N=N—[pyrazolone]—CH₃ (with N-aryl-NO₂ groups and branched azo-pyrazolone with CH₃ and NO₂-phenyl) | (25) | 810 | 8.9 |

Example 13

The elements obtained according to Example 9 through 12 were charged positively by means of a commercially available copying machine. The thus charged elements were then exposed through an original to light, thereby permitting an electrostatic latent image to be formed thereon. This electrostatic latent image was developed using a negatively charged toner-containing dry developer. The thus developed image was electrostatically transferred onto the surface of paper (wood free paper) and fixed, whereby a clear-cut image was obtained. A clear-cut image was obtained likewise in the case of using a wet developer.

Example 14

To 2 parts of Dian Blue (CI 21180) were added 98 parts of tetrahydrofuran. The resulting mixture was pulverized and mixed in a ball mill, thereby obtaining a charge generation pigment solution. This solution was coated onto an aluminum evaporation deposited polyester film by means of a doctor blade and air-dried thereby to form a 1 micron-thick charge generation layer. Subsequently, a charge transport layer forming solution was obtained by mixing 2 parts of anile compound having the structural formula 35, 3 parts of polycarbonate resin (Panlite L available from TEIJIN) and 45 parts of tetrahydrofuran and well dissolving. This solution was coated onto said charge generation layer by means of a doctor blade and the same was dried at 100° C. for 10 minutes, thereby forming a charge transport layer being about 10 microns thick. The element of the instant invention was thus obtained. This element was subjected to −6 KV corona discharge for 20 seconds by means of an electrostatic copying paper tester used in Example 1 and charged negatively. Thereafter, the negatively charged element was left standing in the dark for 20 seconds for measuring the surface potential Vpo (V) at that time, and then was exposed to light from a tungsten lamp so that the surface intensity became 20 lux. Thus, the time (second) required until the surface potential was reduced to half of Vpo was calculated to determine the exposure amount E1/2 (lux·sec). The obtained results showed: Vpo = −1070 V and E1/2 = 9.7 lux·sec.

EXAMPLE 15

A solution consisting of 3 parts of

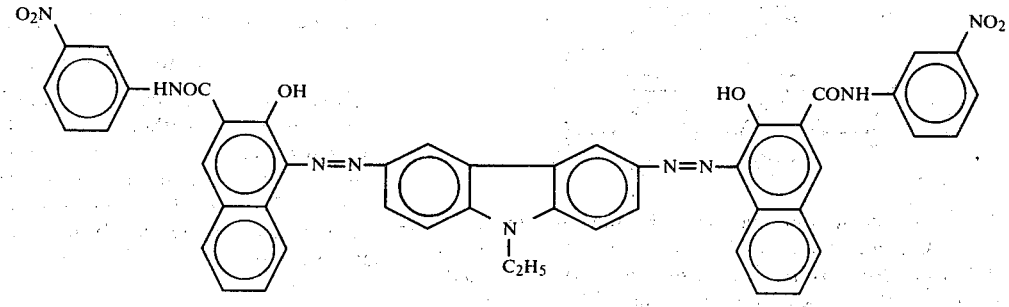

1 part of polyester resin (Polyester Adhesive 49000 available from du Pont) and 96 parts of tetrahydrofuran was pulverized and mixed in a ball mill, thereby obtaining a charge generation pigment dispersion. This dispersion was coated onto an aluminum evaporation deposited polyester film by means of a doctor blade and the same was dried for 5 minutes in a drying machine heated to 80° C., whereby a 1 micron-thick charge generation layer was formed. Subsequently, a charge transport layer forming solution was obtained by mixing 2 parts of anile compound having the structural formula 37, 3 parts of polycarbonate resin (available under the trademark Panlite L from TEIJIN) and 45 parts of tetrahydrofuran and well dissolving. This solution was coated onto said charge generation layer by means of a doctor blade and the same was dried at 100° C. for 10 minutes to thus form a charge transport layer being about 10 microns thick. The element of the instant invention was thus obtained.

This element was charged negatively as in Example 14 and measured as to Vpo and E1/2 with the results: Vpo = −1250 V and E1/2 = 7.1 lux·sec.

EXAMPLE 16 and 17

Elements were prepared in the same manner as Example 15 with the exception that different kinds of charge generation pigments and charge transport materials were employed. The results with such elements were as shown in Table 3.

was coated onto said charge generation layer (selenium evaporation deposited layer) by means of a doctor blade, air-dried and then further dried at a reduced pressure to form thereon a charge transport layer being about 10 microns thick thereon. The element of the instant invention was thus obtained.

This element was measured as to Vpo and E1/2 in accordance with the same procedure as that of Example 14. The obtained results showed that Vpo = −830 V and E1/2 = 3.3 lux·sec.

TABLE 3

| Example | Charge generation pigment | Charge transport material | Vpo | E½ |
|---|---|---|---|---|
| 16 | (structure shown) | 38 | V 670 | lux·sec 2.5 |
| 17 | (structure shown) | 35 | V 830 | 2.1 |

EXAMPLE 18

The elements obtained according to Example 14 through 17 were charged negatively by means of a commercially available copying machine. The thus charged elements were then exposed through an original to light, thereby permitting an electrostatic latent image to be formed thereon. This electrostatic latent image was developed using a positively charged toner-containing dry developer. The thus develped image was electrostatically transferred onto the surface of paper (wood free paper) and fixed, whereby a clear-cut image was obtained.

A clear-cut image was obtained likewise in the case of using a wet developer.

Example 19

Selenium was applied onto an about 300 microns-thick aluminum plate by means of vacuum evaporation method so as to be 1 micron-thick, thereby forming a charge generation layer. Subsequently, 2 parts of anile compound having the structural formula 31, 3 parts of polyester resin (available under the trademark Polyester Adhesive 4900 from du Pont) and 45 parts of tetrahydrofuran were mixed and dissolved to thereby obtain a charge transport layer forming solution. This solution

EXAMPLE 20

In place of the selenium of Example 19 there was employed a perylene type pigment having the following formula:

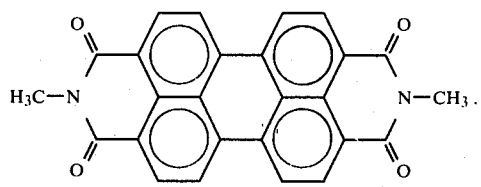

This pigment was coated onto the plate by means of vacuum evaporation method so as to be 0.3 micron thick, thereby forming a charge generation layer. Subsequently, an element similar to that of Example 19 was prepared with the exception that an anile compound having the structural formula 39 was employed as the charge transport material. This element showed the results: Vpo = −810 V and E1/2 = 5.5 lux·sec.

EXAMPLE 21

The elements obtained according to Example 19 and Example 20 were charged negatively by means of a commercially available copying machine. The thus charged elements were then exposed through an original to light, thereby permitting an electrostatic latent image to be formed thereon. This electrostatic latent image was developed with a positively charged toner-containing dry developer. The thus developed image was electrostatically transferred onto the surface of paper (wood free paper) and fixed, whereby a clear-cut image was obtained. A clear-cut image was obtained likewise in the case of using a wet developer.

EXAMPLE 22

A mixture of 1 part of Chlor Dian Blue and 158 parts of tetrahydrofuran was pulverized and mixed in a ball mill. Subsequently, the thus treated mixture was added with 12 parts of anile compound having the structural formula 49 and 18 parts of polyester resin (available under the trademark Polyester Adhesive 49000 from du Pont) and subjected to further mixing, thereby obtaining a photosensitive layer forming solution. This solution was coated onto an aluminum evaporation deposited polyester film by means of a doctor blade and the same was dried at 100° C. for 30 minutes to thereby form a photosensitive layer being about 16 microns thick. The element of this invention was thus obtained.

This element was positively charged with +6 KV corona discharge using the same device as that employed in Example 14 and likewise measured as to Vpo and E1/2 with the results: Vpo=1450 V and E1/2=3.9 lux·sec.

Example 23 through 25

Elements were prepared in accordance with the element preparation method similar to Example 22 with the exception that the charge generation pigment and charge transport material were replaced by those as shown in Table 4. These elements were subjected to the measurements similar to Example 14. The results thus obtained were as shown in Table 4.

TABLE 4

| Example | Charge generation pigment | Charge transport material | Vpo | E½ |
|---|---|---|---|---|
| 23 | [structure with Cl, HNOC, OH, N=N, oxadiazole linker] | 41 | V 870 | lux·sec 7.7 |
| 24 | [structure with HNOC, OH, N=N, fluorenone linker] | 43 | V 910 | 5.9 |
| 25 | [bis-pyrazolone structure with H3C, NO2, CH3 groups] | 46 | 980 | 5.7 |

EXAMPLE 26

The elements obtained according to Example 22 through 25 were charged positively by means of a commercially available copying machine. The thus charged elements were then exposed through an original to light, thereby permitting an electrostatic latent image to be formed thereon. This electrostatic latent image was developed using a negatively charged toner-containing dry developer. The thus developed image was electrostatically transferred onto the surface of paper (wood free paper) and fixed, whereby a clear-cut image was obtained. A clear-cut image was obtained likewise in the case of using a wet developer.

What is claimed is:

1. An electrophotographic element comprising: an electrically conductive substrate, a charge generation layer, a charge transport layer adjacent the charge generation layer, the charge transport layer comprising at least one charge transport compound selected from the group consisting of hydrazone compounds having the following formula (I) and anile compounds having the following formula (II):

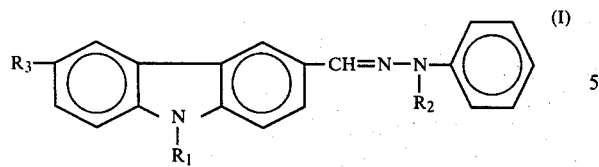
(I)

wherein $R_1$ is methyl, ethyl, 2-hydroxyethyl or 2-chloroethyl; $R_2$ is methyl, ethyl, benzyl or phenyl; and $R_3$ is chlorine, bromine, $C_1$-$C_4$ alkyl, $C_1$-$C_4$ alkoxy, dialkylamino in which the alkyl has 1 to 4 carbon atoms or nitro,

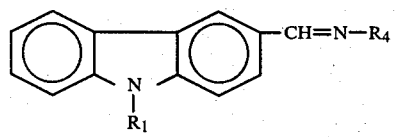
(II)

wherein $R_1$ has the same meaning as defined above, and $R_4$ is substituted phenyl, non-substituted phenyl, naphthyl, a heterocyclic group or $C_1$-$C_{10}$ alkyl;
and a binder agent.

2. An electrophotographic element as claimed in claim 1, wherein said charge transport compound is selected from the group consisting of:

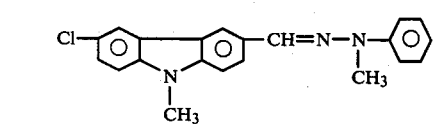
(1)

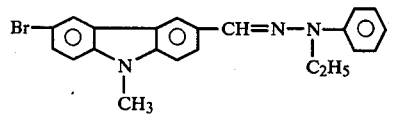
(2)

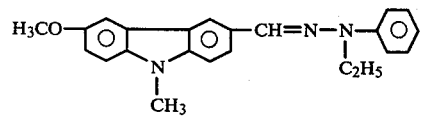
(3)

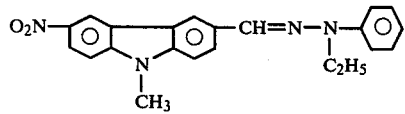
(4)

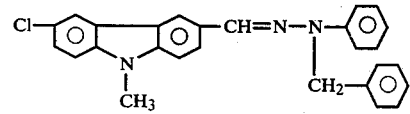
(5)

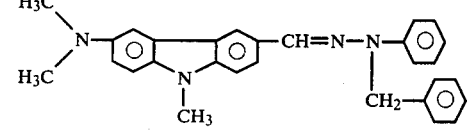
(6)

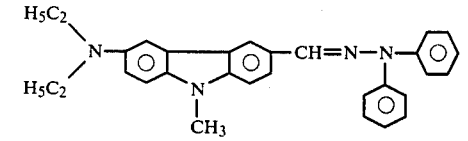
(7)

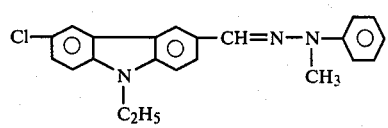
(8)

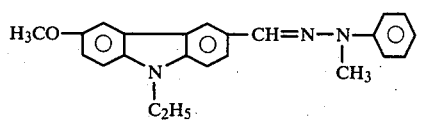
(9)

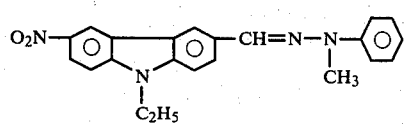
(10)

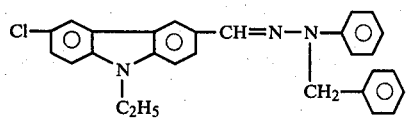
(11)

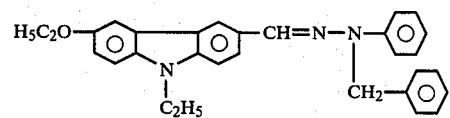
(12)

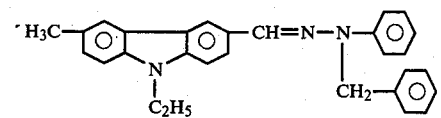
(13)

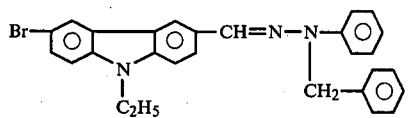
(14)

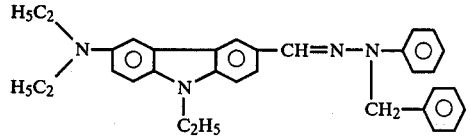
(15)

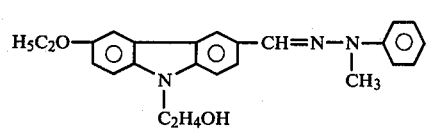
(16)

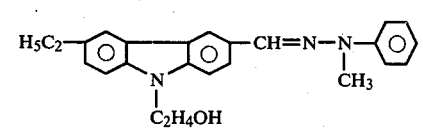
(17)

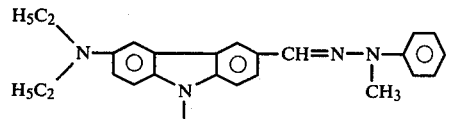
(18)

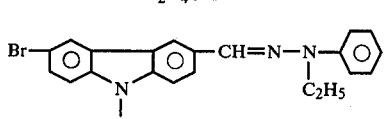
(19)

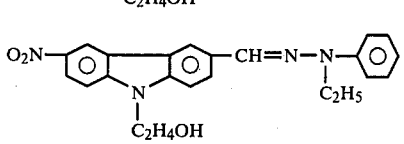
(20)

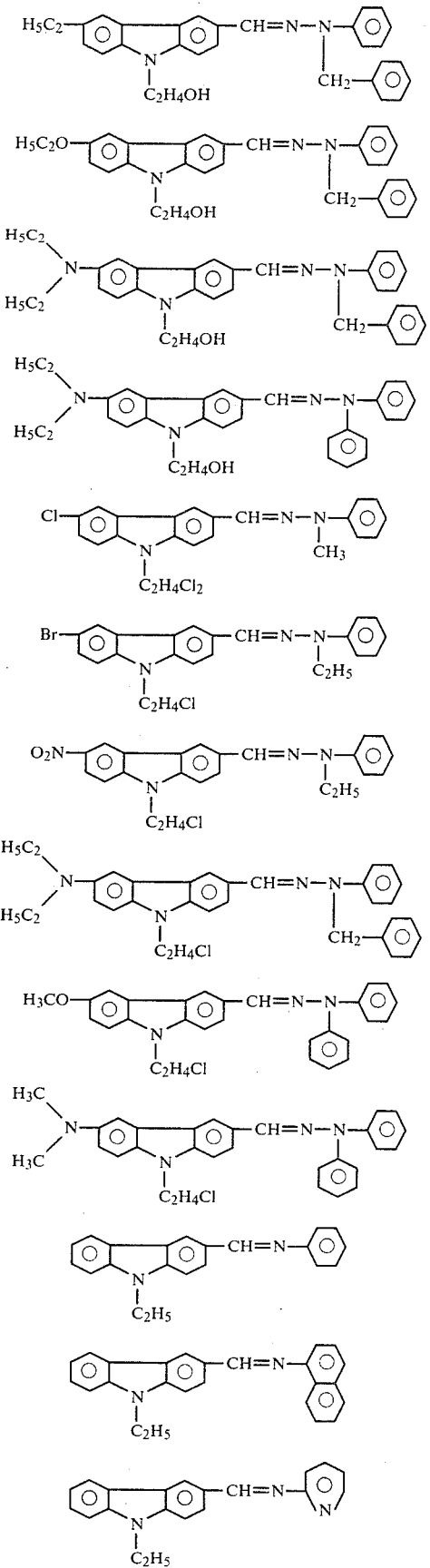
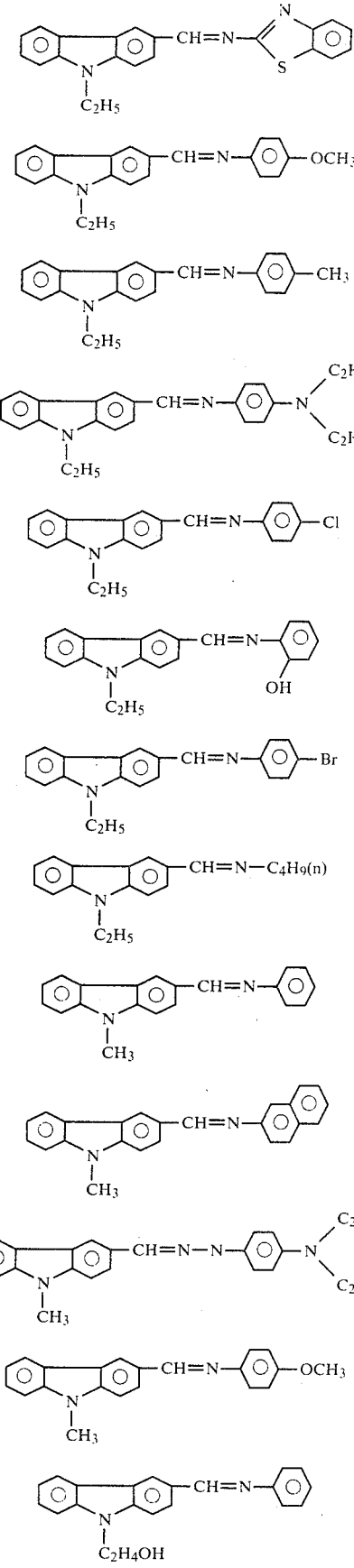

-continued

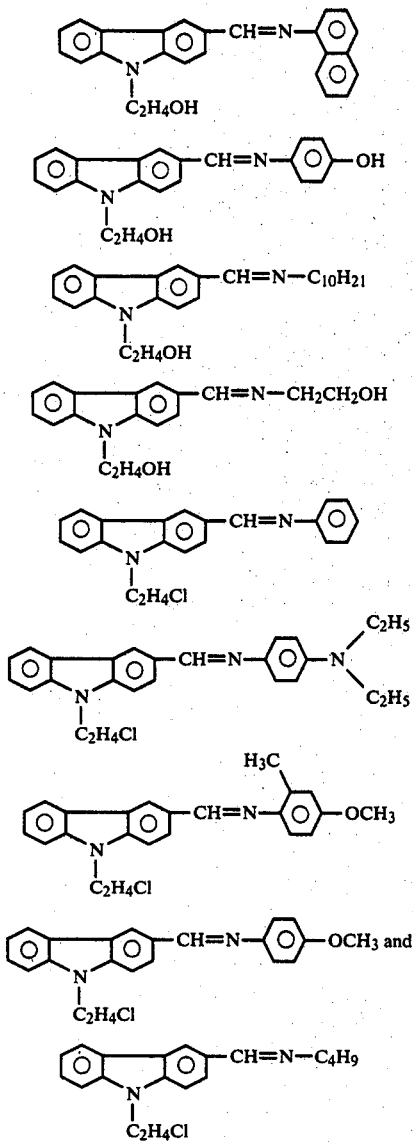

(47)
(48)
(49)
(50)
(51)
(52)
(53)
(54)
(55)

3. An electrophotographic element as claimed in claim 1, wherein said charge transport compound is selected from the group consisting of:

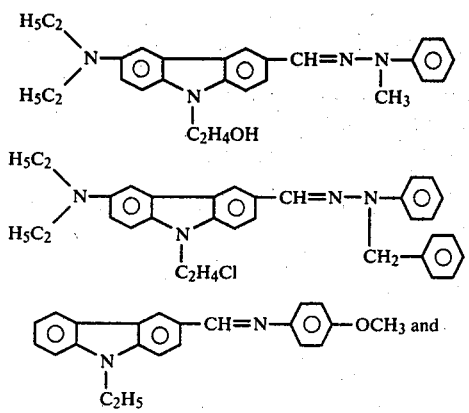

(18)
(28)
(35)

-continued

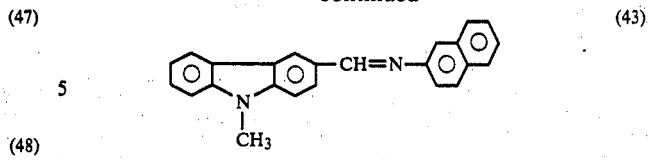

(43)

4. An electrophotographic element as claimed in claim 1, wherein said charge generation layer is positioned between said substrate and said charge transport layer, with said charge transport layer forming an exposed surface of said electrophotographic element.

5. An electrophotographic element as claimed in claim 1 in which said charge generation layer includes a photoconductive material selected from the group consisting of selenium and its alloys, azo pigment, and perylene pigment.

6. An electrophotographic element as claimed in claim 1 in which said binder agent is selected from the group consisting of polyamide, polyurethane, polyester, epoxy resin, polyketone, polycarbonate, polyvinyl ketone, polystyrene, poly-N-vinylcarbazole, polyacrylamide, polyacrylate and mixtures thereof.

7. An electrophotographic element as claimed in claim 1, wherein said charge transport layer is between 5 microns to 20 microns thick.

8. An electrophotographic element as claimed in claim 5 in which said photoconductive material is a material selected from the group consisting of azo pigments having a carbazole group, azo pigments having a styrylstilbene group, azo pigments having a triphenylamine group, azo pigment having a dibenzothiophene group, azo pigments having an oxadiazole group, azo pigments having a fluorenone group, azo pigments having a bis-stilbene group, azo pigments having a distyryloxadiazole group and azo pigments having a distyrylcarbazole group.

9. An electrophotographic element as claimed in claim 7, wherein said photoconductive material is a material selected from the group consisting of azo pigments having a styrylstilbene group.

10. An electrophotographic element as claimed in claim 7, wherein said photoconductive material is 1,4-bis[4-{2-hydroxy3-(2,4-dimethylphenyl)carbamoyl-naphthyl-1}azostyryl-1]benzene.

11. An electrophotographic element as claimed in claim 1 in which said charge generation layer has a thickness of from about 0.01 to about 5 microns, said charge transport layer has a thickness of from about 3 to about 50 microns, said charge transport layer containing from about 10 to about 95% by weight of said charge transport compound and the balance is essentially said binder agent.

12. An electrophotographic element comprising: an electrically conductive substrate; a charge generation layer, which includes a photoconductive material selected from the group consisting of azo pigments having a carbazole group, azo pigments having a styrylstilbene group, azo pigments having a triphenylamine group, azo pigments having a dibenzothiophene group, azo pigments having an oxadiazole group, azo pigments having a fluorenone group, azo pigments having a bis-stilbene group, azo pigments having a distyryloxadiazole group and azo pigments having a distyrylcarbazole group; and a charge transport layer, which comprises at least one charge transport compound selected from the group consisting of hydrazone compounds having the following formula (I) and anile compounds having the following formula (II):

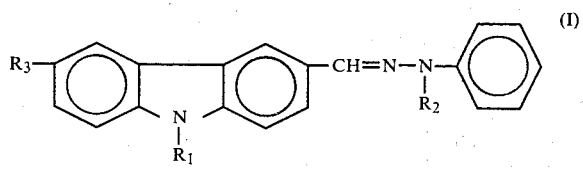

wherein $R_1$ is methyl, ethyl, 2-hydroxyethyl or 2-chloroethyl; $R_2$ is methyl, ethyl, benzyl or phenyl; and $R_3$ is chlorine, bromine, $C_1$–$C_4$ alkyl, $C_1$–$C_4$ alkoxy, dialkylamino in which the alkyl has 1 to 4 carbon atoms or nitro,

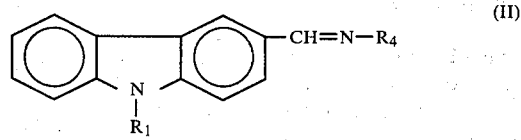

wherein $R_1$ has the same meaning as defined above, and $R_4$ is substituted phenyl, non-substituted phenyl, naphthyl, a heterocyclic group or $C_1$–$C_{10}$ alkyl; and a binder agent.

13. In an electrophotographic element comprising a photoconductive layer and an electrically conductive substrate for supporting said photoconductive layer thereon, the improvement wherein said photoconductive layer contains a binder agent and at least one compound selected from the group consisting of hydrazone compounds having the following formula (I) and anile compounds having the following formula (II):

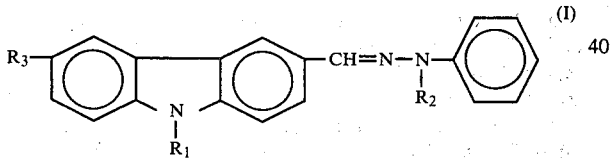

wherein $R_1$ is methyl, ethyl, 2-hydroxyethyl or 2-chloroethyl; $R_2$ is methyl, ethyl, benzyl or phenyl; and $R_3$ is chlorine, bromine, $C_1$–$C_4$ alkyl, $C_1$–$C_4$ alkoxy, dialkylamino in which the alkyl has 1 to 4 carbon atoms or nitro,

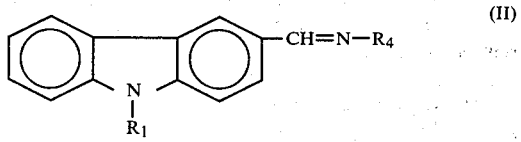

wherein $R_1$ has the same meaning as defined above, and $R_4$ is substituted phenyl, non-substituted phenyl, naphthyl, a heterocyclic group or $C_1$–$C_{10}$ alkyl; and the thickness of said photoconductive layer is in the range of about 3 microns to 50 microns and the content of said hydrazone or anile compound is in the range of about 30 to 70 wt. % in said photoconductive layer.

14. An electrophotographic element as claimed in claim 13, wherein said photoconductive layer further comprises a sensitizer capable of providing said photoconductive layer with a photosensitivity in the visible light range, the content of said sensitizer is in the range of about 0.1 to 5 weight percent in said photoconductive layer, and said sensitizer is a compound selected from the group consisting of triarylmethane dye, xanthene dye, cyanine dye, and pyrylium dye.

15. An electrophotographic element as claimed in claim 13, further comprising an adhesive layer or a barrier layer between said substrate and said photoconductive layer.

16. An electrophotographic element as claimed in claim 13, wherein said photoconductive layer further comprises a plasticizer selected from the group consisting of halogenated paraffin, polybiphenyl chloride, dimethylnaphthalene and dibutyl phthalate.

17. In an electrophotographic element comprising a photoconductive layer and an electrically conductive substrate for supporting said photoconductive layer thereon, the improvement wherein said photoconductive layer comprises: a charge transport medium comprising a binder agent, a charge transport compound selected from the group consisting of hydrazone compounds having the following formula (I) and anile compounds having the following formula (II):

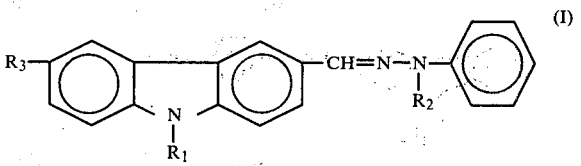

wherein $R_1$ is methyl, ethyl, 2-hydroxyethyl or 2-chloroethyl; $R_2$ is methyl, ethyl, benzyl or phenyl; and $R_3$ is chlorine, bromine, $C_1$–$C_4$ alkyl, $C_1$–$C_4$ alkoxy, dialkylamino in which the alkyl has 1 to 4 carbon atoms or nitro,

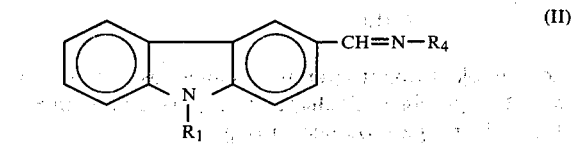

wherein $R_1$ has the same meaning as defined above, and $R_4$ is substituted phenyl, non-substituted phenyl, naphthyl, a heterocyclic group or $C_1$–$C_{10}$ alkyl; and a charge generation material dispersed in said charge transport medium, the thickness of said photoconductive layer being in the range of about 3 microns to 50 microns, the content of said charge transport compound being in the range of about 10 to 95 weight percent in said photoconductive layer, and the content of said charge generation material being in the range of about 0.1 to 50 weight percent in said photoconductive layer.

* * * * *

UNITED STATES PATENT AND TRADEMARK OFFICE
CERTIFICATE OF CORRECTION

PATENT NO. : 4 297 426

DATED : October 27, 1981

INVENTOR(S) : Kiyoshi Sakai et al

It is certified that error appears in the above—identified patent and that said Letters Patent is hereby corrected as shown below:

Column 26, line 26; change "claim 1" to ---claim 11---.

Column 26, line 45; change to read as follows:
   ---bis[4-{2-hydroxy-3-(2,4-dimethylphenyl)carbamoyl- ---.

Signed and Sealed this

Eighteenth Day of May 1982

[SEAL]

Attest:

GERALD J. MOSSINGHOFF

Attesting Officer

Commissioner of Patents and Trademarks